(12) United States Patent
Han et al.

(10) Patent No.: US 7,280,921 B2
(45) Date of Patent: Oct. 9, 2007

(54) METHOD FOR VISUALIZING LARGE-SCALE PROTEIN INTERACTION DATA

(75) Inventors: Kyungsook Han, Incheon (KR); Byong-Hyon Ju, Incheon (KR)

(73) Assignee: Inha University Foundation, Inha University (KR)

( * ) Notice: Subject to any disclaimer, the term of this patent is extended or adjusted under 35 U.S.C. 154(b) by 207 days.

(21) Appl. No.: 10/290,432

(22) Filed: Nov. 7, 2002

(65) Prior Publication Data

US 2004/0059521 A1 Mar. 25, 2004

(30) Foreign Application Priority Data

Sep. 23, 2002 (KR) .................. 10-2002-0057604

(51) Int. Cl.
*G06F 17/11* (2006.01)
*G06F 17/50* (2006.01)

(52) U.S. Cl. .......................................... 702/19; 703/11
(58) Field of Classification Search ................... 702/19, 702/20; 703/11; 707/102
See application file for complete search history.

(56) References Cited

OTHER PUBLICATIONS

An article entitled "SCOP: A Structural Classification of Proteins Database . . . ", By Murzin et al., published in J. Mol. Biol. (1995) 247, pp. 536-540.
An article entitled "Generating Protein Interaction Maps . . . ", By Lappe et al., published in vol. 17 Suppl. 1 2001, pp. S149-S156.
An article entitled "A Java Applet for Visualizing . . . ", By Ralf Mrowka, published in Bioinformatics Applications Note, vol. 17, No. 7, 2001, pp. 669-670.
An article entitled "A Network of Protein-Protein Interactions in Yeast", By Schwikowski et al., published in Nature Biotechnology, vol. 18, Dec. 2000, pp. 1257-1261.
An article entitled "Towards an Understanding of Complex Protein Networks", By Tucker et al., published in Trends in Cell Biology, vol. 11, No. 3, Mar. 2001, pp. 102-106.
An article entitled, "A Comprehensive Analysis of Protein-Protein . . . ", By Uetz et al., published in Nature, vol. 403, Feb. 10, 2000, pp. 623-629. This.
An article entitled "Mapping Protein Family Interactions: Intramolecular . . . ", By Park et al., published in J. Mol. Biol. (2001), 307, pp. 929-938.

(Continued)

*Primary Examiner*—Michael Borin
(74) *Attorney, Agent, or Firm*—Bachman & LaPointe, P.C.

(57) ABSTRACT

Disclosed is a method of visualizing large-scale protein interaction data, comprising the steps of (1) producing an initial layout by placing all nodes of protein interaction data on the surface of a sphere by increasing horizontal and vertical angles of polar coordinates; and (2) yielding a graph by iterating a process moving each node of the initial layout to an equilibrium position considering global spring forces between non-adjacent nodes as well as local spring forces between adjacent nodes on a predetermined number of times, by which large-scale protein interaction data is effectively visualized in a three-dimensional space. The method for visualization of the present invention, which is much faster than the conventional algorithms, can be used for interactive analysis, as well as provide an integrated system capable of directly visualizing query results from a protein-protein interaction database.

4 Claims, 15 Drawing Sheets

OTHER PUBLICATIONS

An article entitled "Tulip", By Auber David, published in GD 2001, LNCS 2265, pp. 435-437, 2002.

An article entitled "A Multilevel Algorithm for Force-Directed Graph Drawing", By C. Walshaw, published in GD 2000, LNCS 1984, pp. 171-182, 2001.

An article entitled "Pajek-Analysis and Visualization . . . ", By Batagelj et al., published in GD 2001, LNCS 2265, pp. 477-478, 2002.

An article entitled "An Algorithm for Drawing General Undirected Graphs", By Kamada et al., published in Information Processing Letters, Department of Information Science, Faculty of Science, University of Tokyo, Apr. 1989, pp. 7-15.

FIG. 1

Algorithm 1 Layout

1: $r = 1$
2: repeat
3:     $g = 0.01 \cdot r \cdot k^2$     {k: natural spring length}
4:     for $v \in V$ do
5:         $D = 0$     {D: displacement vector of v}
6:         for $u \in V, u \neq v$ do
7:             $\Delta = pos[u] - pos[v]$
                {pos[u]: position of vertex $u$}
8:             $D = D - g \cdot (\Delta/|\Delta|) \cdot (|u|/|\Delta|)$
                {|u|: distance of $u$ from the origin}
9:             if $u \in \Gamma(v)$ then
10:                 $D = D - \Delta/|\Delta| \cdot (1 - |\Delta|/k)/|\Gamma(v)|$
                {$\Gamma(v)$: set of vertices adjacent to $v$}
11:             end if
12:         end for
13:         $pos[v_{new}] = pos[v_{old}] + D$
14:     end for
15:     $r = 0.98 \cdot r$
16: until $T$ times
        {T: user-specified number or 20 by default}

FIG. 4

| Algorithm 2 InitialLayout | |
|---|---|
| 1: $\theta_{increment} = 2\pi/\sqrt{n}$ | {$n$: number of nodes} |
| 2: $\phi_{increment} = 2\pi/n$ | |
| 3: $\theta = 0, \phi = 0$ | |
| 4: for $v \in V$ do | |
| 5: $\quad pos[v] = (r, \theta, \phi)$ | {$r$: radius of a sphere} |
| 6: $\quad \theta = \theta + \theta_{increment}$ | |
| 7: $\quad \phi = \phi + \phi_{increment}$ | |
| 8: end for | |

METHOD FOR VISUALIZING LARGE-SCALE PROTEIN INTERACTION DATA

BACKGROUND OF THE INVENTION

1. Field of the Invention

The present invention relates to a method of visualizing protein interaction data into a three-dimensional graph.

2. Description of the Prior Art

With recent developments in proteomics, protein-protein interaction data are rapidly increasing in quantity. Because of being large-scale, the data can be more easily understood when being expressed into graphs rather than a long list of interacting proteins. In this regard, active research on methods to visualize protein interaction networks has been conducted. However, it is not easy to visualize protein interaction data, for the following reasons: first, the data yields a complex non-planar graph with a large number of edge crossings; and second, when visualized as a graph, the data often yields a disconnected graph comprising many connected components.

Most graph-drawing tools use modified force-directed layout algorithms which have flexibility, are easily implemented, and produce good drawing results. The conventional force-directed layout algorithms first place nodes randomly, and then rearrange their positions through optimization methods to find a layout with minimum energy. Force-directed layout algorithms differ mainly in selecting energy function and minimization methods. Examples of force-directed layout algorithms include algorithms by Kamada & Kawai (1989) and Fruchterman & Reingold (1991). The algorithm by Kamada & Kawai produces a two-dimensional graph and cannot produce a disconnected graph. A large number of force-directed algorithms share a common problem of being too slow in treating large-scale graphs because of computing a force between every pair of nodes at each iteration step.

Based on a relaxation algorithm, a java applet program was developed by Mrowka (2001) for visualization of protein interactions, and was tested on yeast two-hybrid (Y2H) data (Uetz et al., 2000). However, this program has several disadvantages as follows. The program requires all protein interaction data to be provided as parameters of the applet program in html sources. There is no way to save a visualized graph except by capturing the window. Also, images captured from the window are static and typically of low quality, and cannot be refined or changed later to reflect an update in data. Further, a user can move a node, but cannot select or save a connected component containing a specific protein for further use.

Some visualization tools of protein interactions use general-purpose drawing tools, instead of their own algorithms or programs developed for visualization of protein interactions. For example, PSIMAP (Park et al., 2001; and Lappe et al., 2001) displays interactions between protein families by comparing Y2H data with DIP data using structural classification of proteins (Murzin et al., 1995). It was produced by Tom Sawyer software (www.tomsawyer.com) and then refined through manual work to remove edge crossings.

A research group at the University of Washington (Schwikowski et al., 2000; and Tucker et al., 2001) tried to visualize Y2H data using AGD (www.mpi-sb.mpg.de/AGD/), which is another general-purpose drawing tool. Because of being a general-purpose drawing tool, despite being powerful, AGD does not provide a function required for studying protein-protein interactions. For example, most protein interaction data including Y2H data yields a disconnected graph consisting of many connected components, which is also a non-planar graph with a large number of edge crossings not removable in a two-dimensional drawing. The graph can be analyzed by working on individual connected components or subgraphs containing a specific protein. Alternatively, the non-planar graph can be visualized into a three-dimensional graph with no edge crossings. However, because AGD doesn't provide these functionalities, it is difficult to analyze the graph.

The graph-drawing programs are problematic in terms of not querying a database and directly visualizing query results from the database. Since they require input data in a specific format for visualization, a user has to convert data into the format. In addition, protein interaction data is generally updated with the passage of time, but the conventional programs cannot reflect the updated data on the visualization.

The conventional graph-drawing tools have problems in visualizing protein interactions as follows. They draw a complex graph with a large number of edge crossings or a static graph difficult to revise. Also, they are too slow in performing interactive work with a large volume of data. Further, they can visualize protein interaction data only when the data is input in a specific format, because of not being capable of directly reading data from a protein interaction database.

SUMMARY OF THE INVENTION

To solve the problems encountered in the prior art, it is the objective of the present invention to provide a new method of visualizing large-scale protein interaction networks into a three-dimensional drawing. In more detail, the present invention aims to provide a new force-directed algorithm capable of visualizing protein interactions at a faster speed than the conventional algorithms, being used in interactive analysis, directly visualizing query results from a protein interaction database in a three-dimensional space, and revising or navigating visualized networks at a later time.

BRIEF DESCRIPTION OF THE DRAWINGS

The above and other objectives, features and other advantages of the present invention will be more clearly understood from the following detailed description taken in conjunction with the accompanying drawings, in which:

FIG. 1 describes algorithm Layout of a method for visualization according to the present invention;

FIG. 4 describes an algorithm for initial layout;

DESCRIPTION OF THE PREFERRED EMBODIMENTS

Figure 2A:
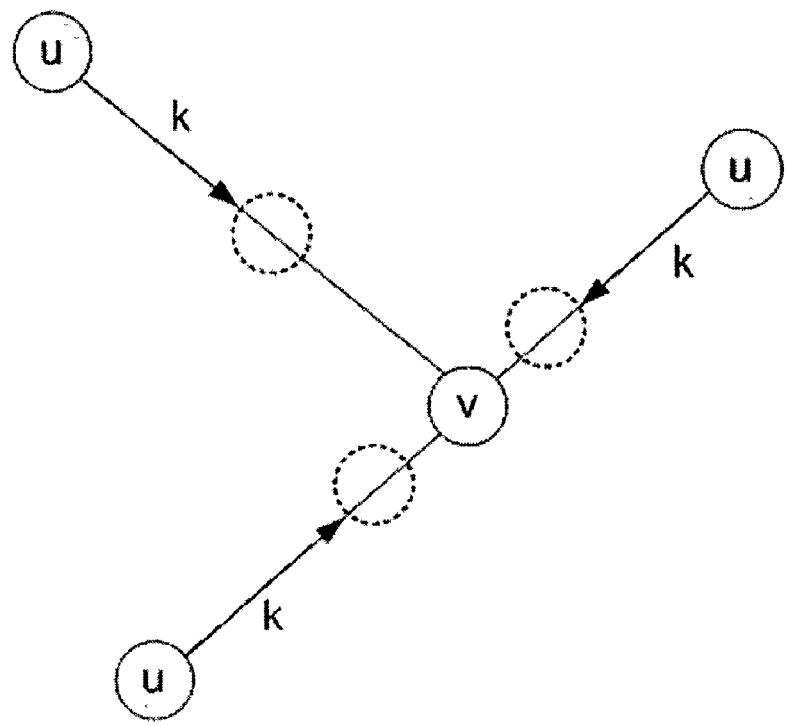
FIGS. 2a and 2b show displacements of a node v due to local forces between adjacent nodes.

The present invention is directed to a method of visualizing effectively large-scale protein interaction data on a display by use of a computer, which yields a graph using proteins as nodes and interactions between proteins as edges, comprising the steps of (1) producing an initial layout by placing all proteins of protein interaction data as nodes on the surface of a sphere by increasing a horizontal angle (theta) and a vertical angle (phi) of each node in polar coordinates as described in the following algorithm:

```
1: θ_increment = 2π/√n       {n: number of nodes}
2: φ_increment = 2π/n
3: θ = 0, φ = 0
4: for v ∈ V do
5:   pos[v] = (r, θ, φ)       {r: radius of a sphere}
6:   θ = θ + θ_increment
7:   φ = φ + φ_increment
8: end for;
``` and (2) yielding a three dimensional graph by iterating a predetermined number of times of process moving each node of the initial layout to equilibrium position and updating node positions based on spring forces between non-adjacent nodes and the node of the initial layout as well as spring forces between adjacent nodes and the node of the initial layout, wherein the three-dimensional graph is yielded through the following algorithm:

```
1: r = 1
2: repeat
3:   g = 0.01 · r · k²          {k: natural spring length}
4:   for v ∈ V do
5:     D = 0                    {D: displacement vector of v}
6:     for u ∈ V, u ≠ v do
7:       Δ = pos[u] − pos[v]    {pos[u]: position of node u}
8:       D = D − g · (Δ/|Δ|) · (|u|/|Δ|)
                                {|u|: distance of u from the origin}
9:       if u ∈ Γ(v) then
10:        D = D − Δ/|Δ| · (1 − |Δ|/k)/|Γ(v)|
                                {Γ(v): set of nodes adjacent to v}
11:      end if
12:    end for
13:    pos[v_new] = pos[v_old] + D
14:  end for
15:  r = 0.98 · r
16: until T times              {T: user-determined number or 20 by default}.
```

In accordance with the present invention, the method is characterized in that the number of the iteration of Step 2 can be changed by a user, and of communicating with database storing the protein interaction data.

In addition, the method further comprises the step (Step 3) of simplifying the graph by limiting distance level of neighboring nodes to a predetermined distance, for nodes selected by a user.

Protein-protein interaction data can be visualized as a graph in which nodes represent proteins and edges represent protein-protein interactions. The degree of a node is the number of its edges. An edge (u,v) with u=v is a self-loop. Protein interaction data are featured as follows: (1) when visualized into a graph, the data yields a disconnected graph with many connected components. For example, MIPS genetic interaction data (mips.gsf.de/proj/yeast/tables/interaction) contains over 100 connected components; (2) the data generates a non-planar graph with a large number of edge crossings that cannot be removed in a two-dimensional graph; (3) since different proteins have very different numbers of interacting proteins within a set of data, a graph visualizing the data contains nodes of very high degree as well as nodes of a low degree of interaction; (4) the data often contains protein interactions corresponding to self-loops; and (5) the data contains multiple interactions for an identical protein pair of proteins.

In accordance with the present invention, the interactions corresponding to self-loops are stored in the edge table of the database, but ignored during visualization in order to simplify the drawing process and produce clear graphs. If the original protein interaction database contains multiple entries for an identical edge, the interactions are stored once in a local database. Protein interaction networks visualized by the program according to the present invention can be stored in an image file, the local database or a text file in GML format (Himsolt, 1997). GML (Graph Modeling Language) is a portable graph file format. Saving a graph in GML format is advantageous in terms of reviewing a previously calculated graph by loading its GML file.

The conventional force-directed algorithms have a common problem of being very slow when dealing with large-scale graphs. Therefore, the present invention provides a method of visualizing large-scale protein interaction data through a new force-directed algorithm capable of significantly improving the speed dealing with data and the visual clarity of graphs. Based on Walshaw's algorithm (2000), the method for visualization according to present invention is obtained by modifying Walshaw's algorithm.

FIG. 1 describes a layout algorithm according to the present invention. Walshaw's algorithm is problematic in terms of not yielding a desired result when a graph contains a dense subgraph with nodes of very high degree. Walshaw's algorithm iteratively computes node positions until size of the graph falls below a certain threshold value, thus causing unnecessary iteration of the algorithm without improving the entire layout. Therefore, the algorithm according to the present invention employs a different termination condition from Walshaw's algorithm, which is 20 iterations by default. The value of 20 was selected empirically based on comparative experiments, and the number of the iterations can be increased through a user interface (line 16).

At each loop, the node positions are updated based on global spring forces between non-adjacent nodes (line 8) as well as local spring forces between adjacent nodes (line 10).

Figure 2B:
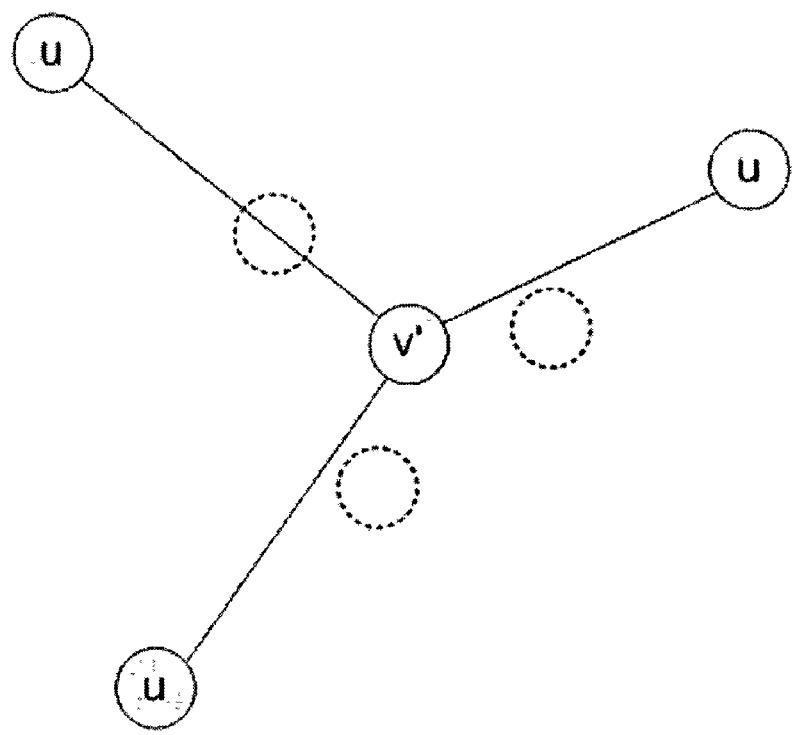

FIGS. 2a and 2b show displacements of a node v due to local forces between adjacent nodes. As shown in FIG. 2a, node v is connected to 3 nodes, and the force on v from any one (u) of the 3 adjacent nodes moves v along the line passing through v and u. The aggregate force imposed by all adjacent nodes moves v to the equilibrium position, as shown in FIG. 2b.

Figure 3:
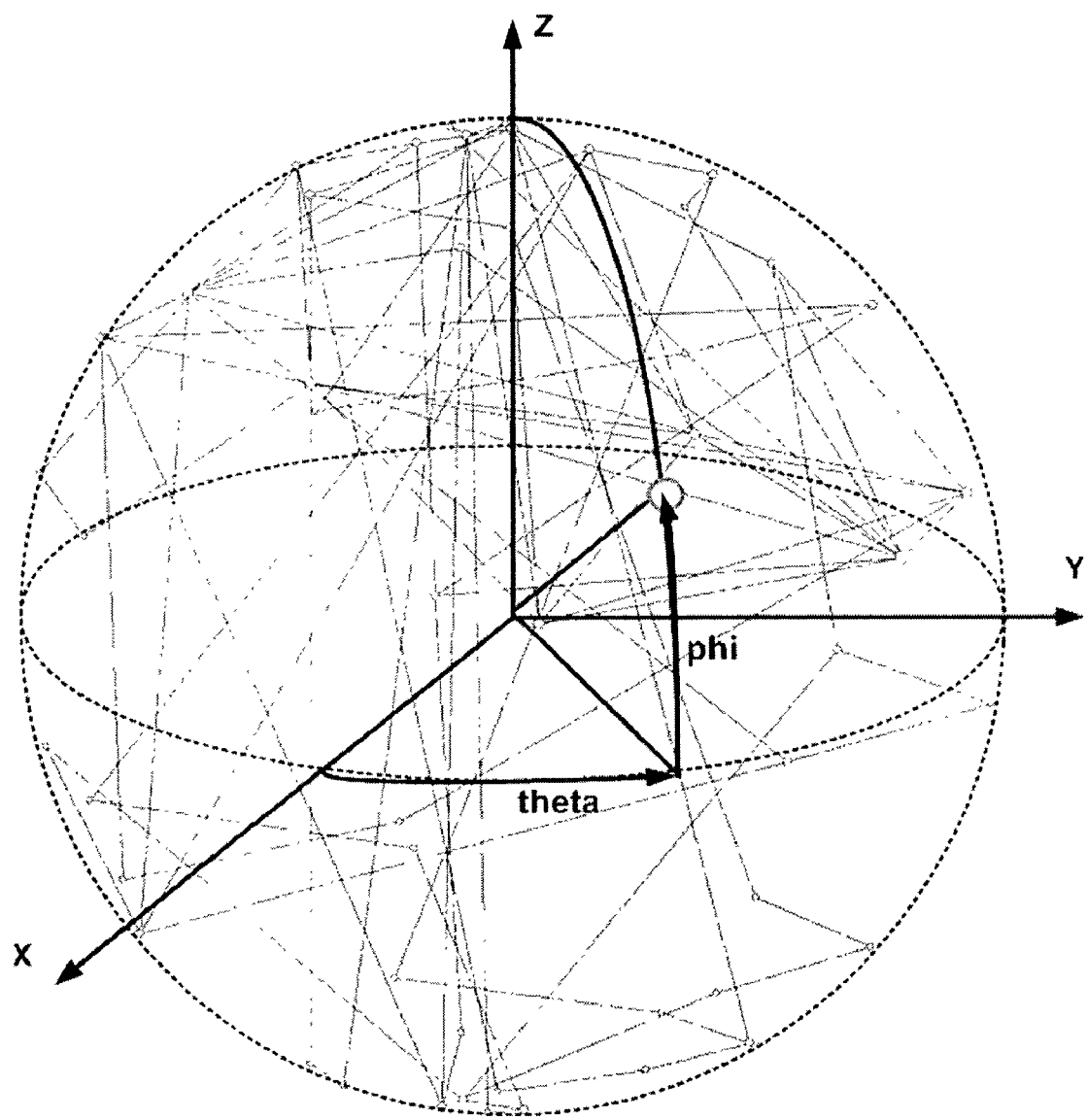
FIG. 3 illustrates an example of an initial layout for a graph with 473 nodes.

The present invention employs an algorithm for initial layout. The conventional force-directed graph drawing algorithms begin by randomly placing all nodes of a graph in a two-dimensional plane or three-dimensional space, and then successively refines an initial layout by optimization methods to find a layout with the minimum energy. When the initial layout contains overlapping nodes or nodes in the same plane, the computation to relocate them is often increased. Thus, a different approach not randomly placing nodes for the initial layout and not requiring much time was employed in the present invention. In accordance with the present invention, nodes are placed on the surface of a sphere by increasing both the horizontal and vertical angles of polar coordinates. This method minimizes the number of times of placing nodes in a plane. FIG. 3 illustrates an example of an initial layout for a graph with 473 nodes, while an algorithm for initial layout is outlined in FIG. 4.

The computational cost of the algorithm according to the present invention was analyzed as follows. For a graph with n(number of nodes)=V, an initial layout takes only $O(n)$ time, and does not affect the global time complexity of the algorithm. Let T be the total number of iterations of the outer loop (line 2 in FIG. 1). $O(n)$ time is required to compute the displacement D of a node, and $O(n^2)$ is required to compute the displacement D of all nodes at each step of the outer loop. Therefore, the required total time is $O(T \cdot n^2) = O(n^2)$, in which T is a constant. Thus, the algorithm according to the present invention is much faster than a spring-embedder algorithm by Kamada & Kawai (1989) with the time complexity $O(n^3)$.

Figure 5:
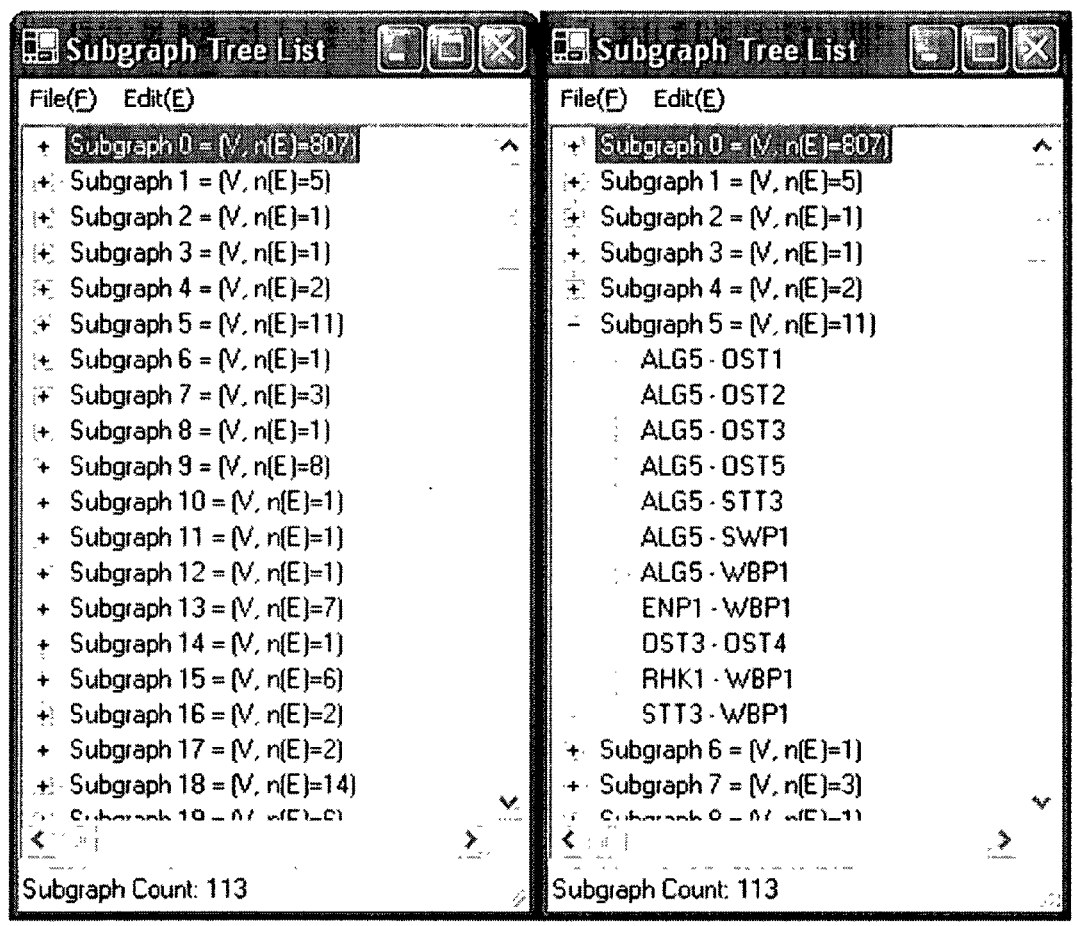
FIG. 5 is a subgraph tree list.
Figure 12:
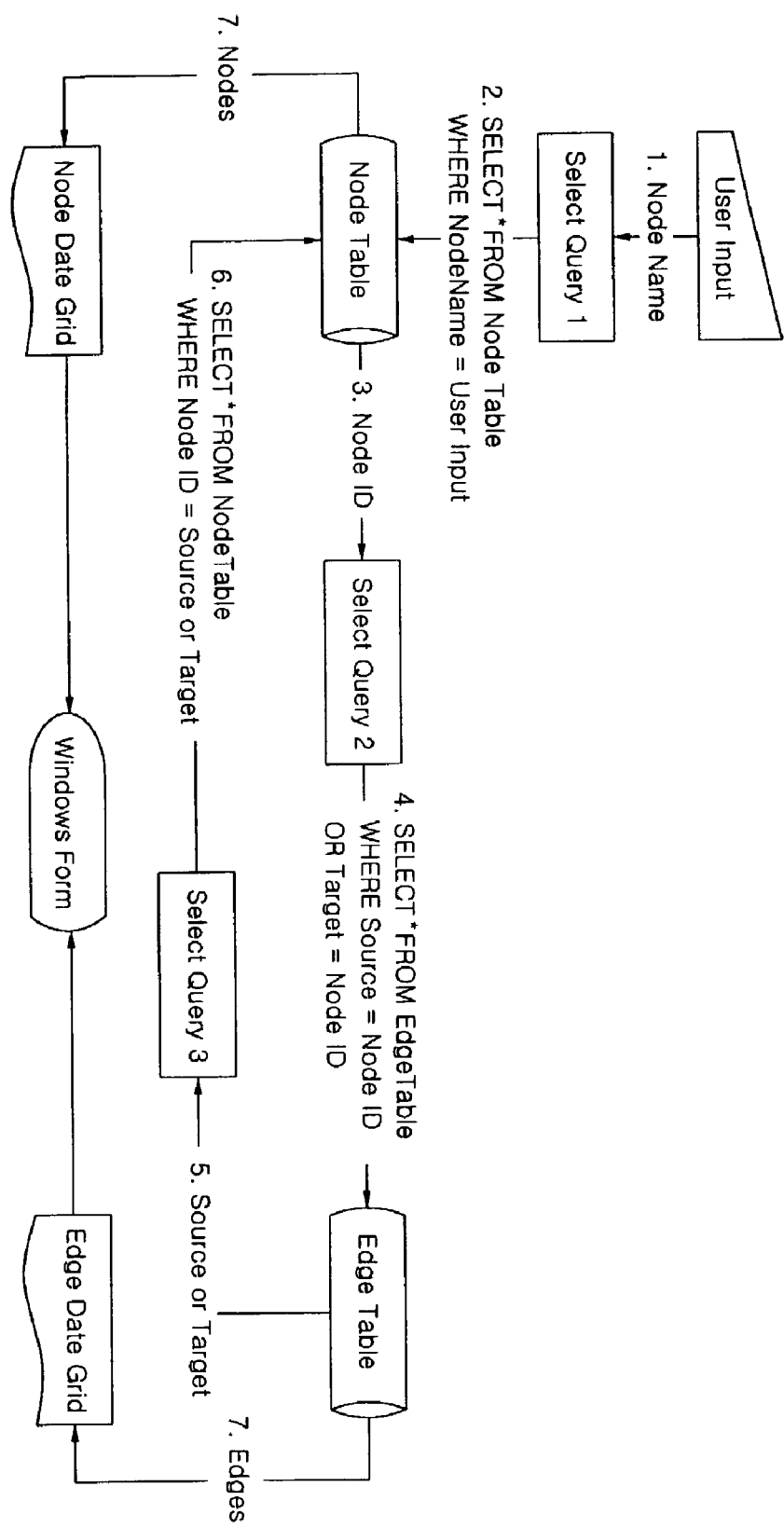
FIG. 12 is a process of finding connected components.

In a drawing tool implemented using the method for visualization according to the present invention, it is possible to find subgraphs and then work on individual subgraphs. Due to the size or nature of protein interaction networks, it should be possible to find subgraphs (such as connected components of a disconnected graph or subgraphs of proteins interacting with a certain protein) and to work on individual subgraphs. The procedure of finding a connected component can be applied to all nodes to obtain a complete list of connected components (see, FIG. 12). As shown in FIG. 5 for an example, the list shows the total number of connected components as well as the size, nodes and edges of each connected component.

In addition, since protein interaction data is large-volume and may be modified with the passage of time, a database is more effective in maintaining the data than flat files. Therefore, local databases of protein interaction data were constructed in the present invention.

Figure 6:
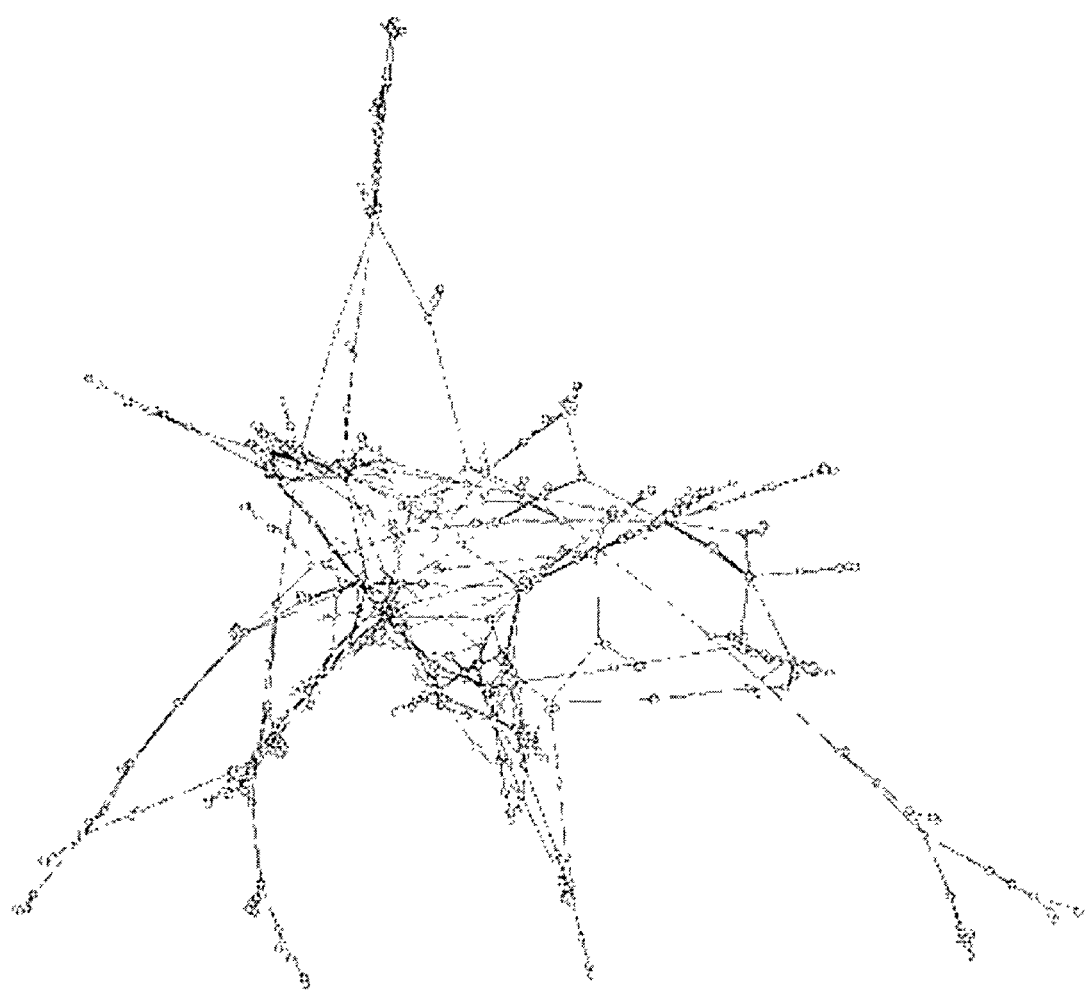
FIG. 6 illustrates the result of drawing a subgraph O of FIG. 5 in a three-dimensional space.

The method for effective visualization of large-scale protein interaction data according to the present invention was implemented in a program called InterViewer. FIG. 5 lists the connected components of MIPS genetic interaction data, which contains 1093 interactions between 888 proteins, excluding multiple interactions between an identical pair of proteins. The left window shows all connected components of MIPS genetic interaction data. When a user clicks a connected component, all edges of the connected components are displayed on the right window. Among the connected components, subgraph O is the largest with 531 nodes and 807 edges, as well as 2 self-loops. FIG. 6 displays subgraph O visualized by InterViewer, which seems to have edge crossings, but actually has no edge crossing when being visualized into a three-dimensional drawing on a video monitor.

Figure 7:
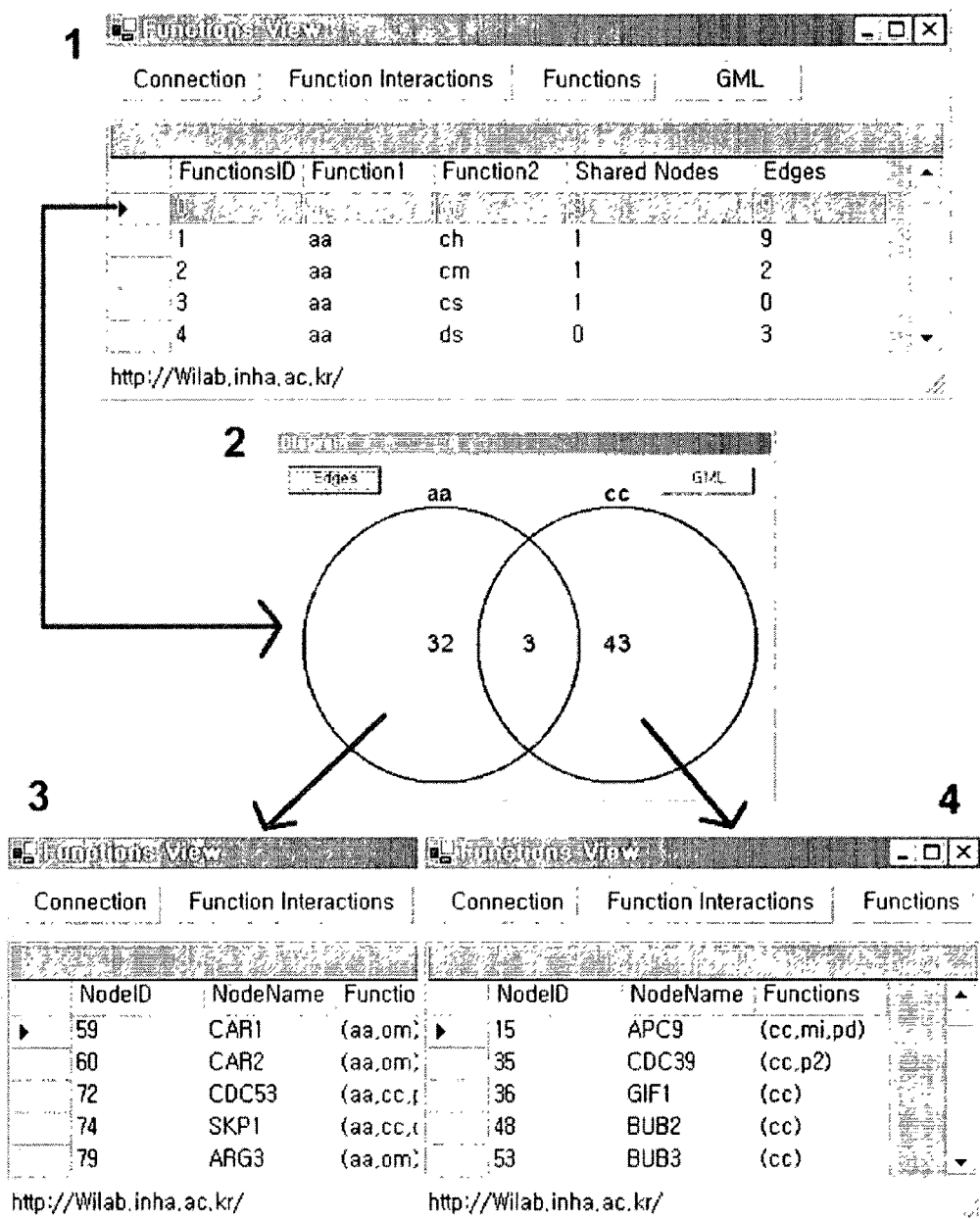
FIG. 7 shows an example of analysis of protein-protein interaction.

The program InterViewer allows a user to analyze protein-protein interactions and explore three-dimensional drawings by rotating or zooming in or out. FIG. 7 shows an example for analysis of protein-protein interactions, in which the first window shows the number of proteins common in every pair of function groups and the number of internal interactions in each group. If the user clicks a row in the first window, the relation of proteins and function groups is shown in a Venn diagram. The diagram in the second window indicates that 35 proteins have the function 'aa' (amino-acid metabolism), 46 proteins have the function of 'cc' (cell cycle control), and 3 proteins have both of the functions 'aa' and 'cc'. If the user clicks a certain function group, all proteins of the function group are listed, as shown in the third and fourth windows.

Figure 8:
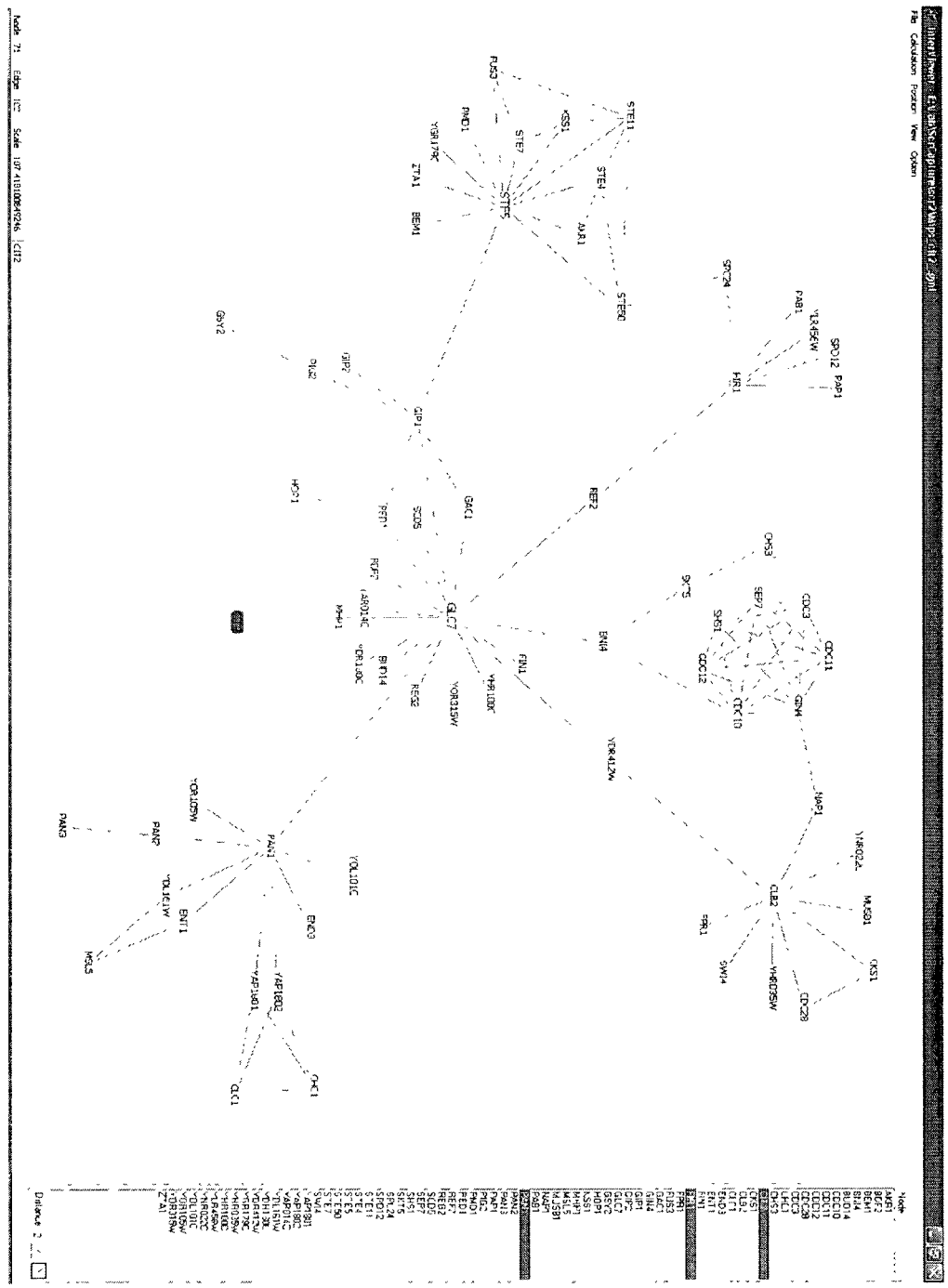
FIG. 8 is a simplified graph of FIG. 6.
Figure 9A:
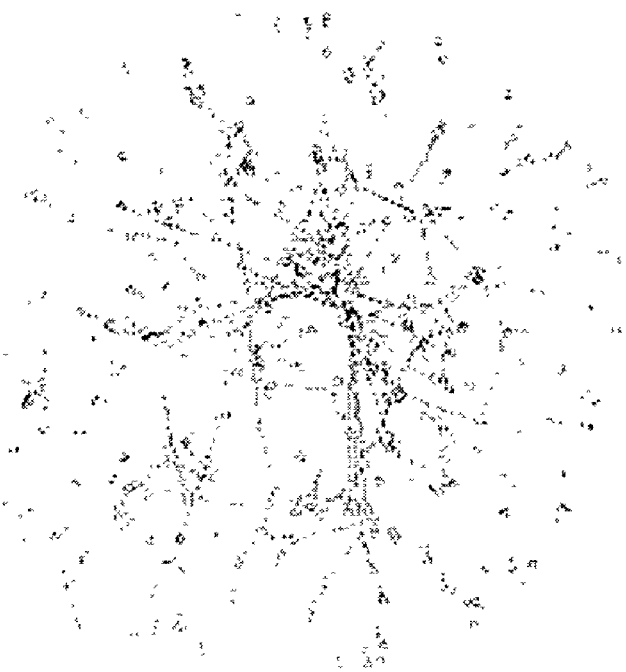
FIGS. 9a to 9d illustrate results of visualizing Y2H data, by InterViewer (FIG. 9a), Pajek (Fruchterman and Reingold's layout) (FIG. 9b), Tulip (GEM layout) (FIG. 9c), and Tulip (Speing-Electrical Force layout) (FIG. 9d)
Figure 9B:
Figure 9C:
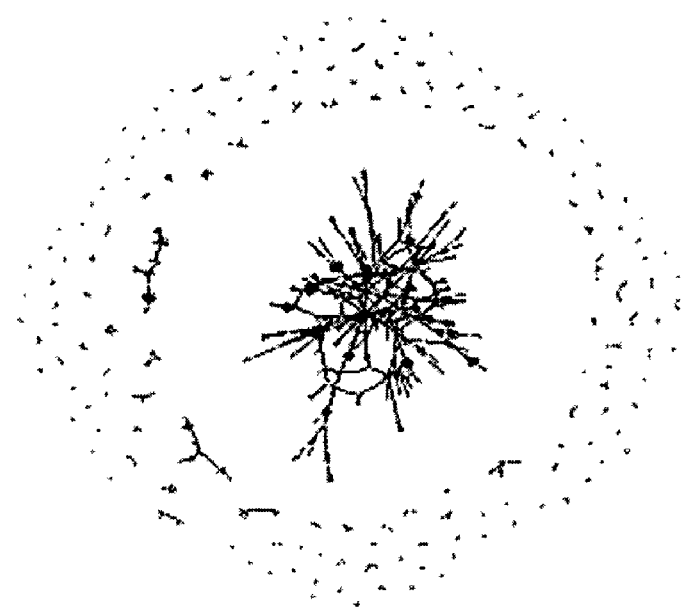
Figure 9D:
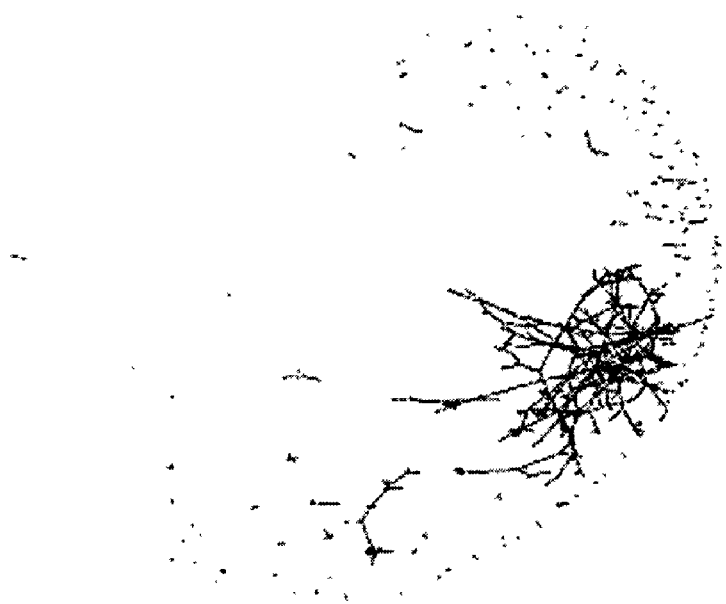
Figure 10A:
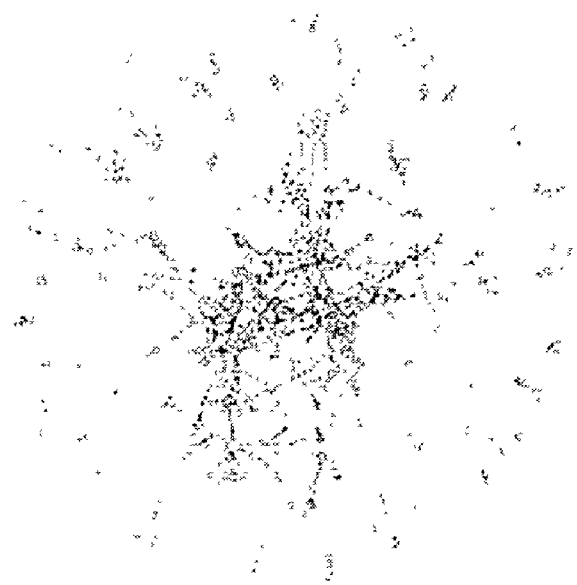
FIGS. 10a to 10d illustrate results of visualizing MIPS genetic interaction data, by InterViewer (FIG. 10a), Pajek (Fruchterman and Reingold's layout) (FIG. 10b), Tulip (GEM layout) (FIG. 10c), and Tulip (Speing-Electrical Force layout) (FIG. 10d)
Figure 10B:
Figure 10C:
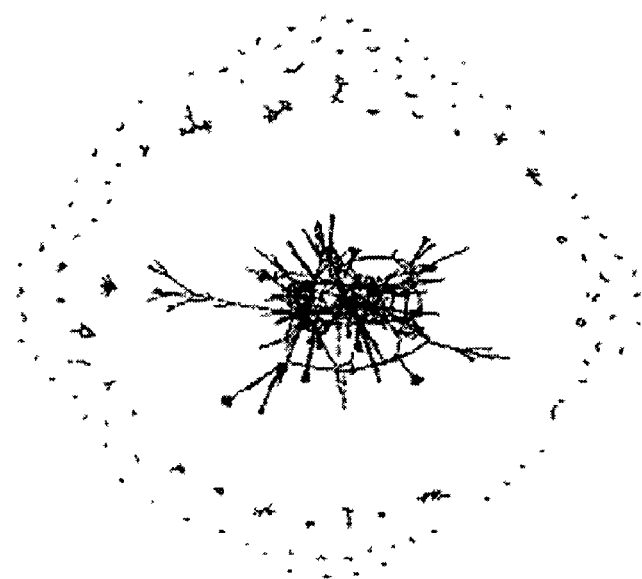
Figure 10D:
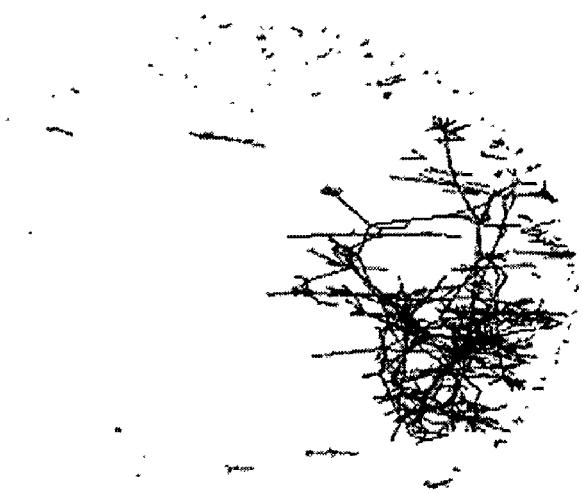
Figure 11A:
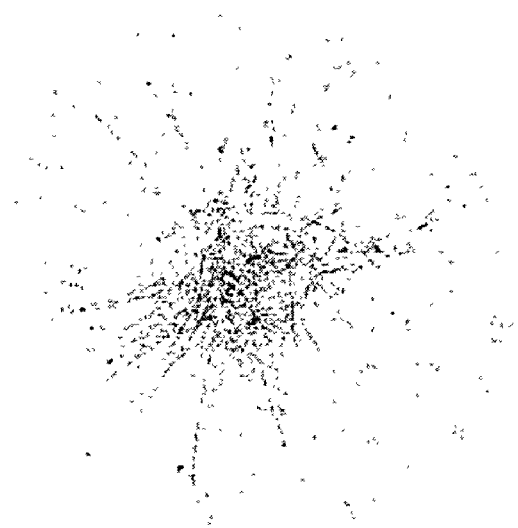
FIGS. 11a to 11d illustrate results of visualizing MIPS physical interaction data, by InterViewer (FIG. 11a), Pajek (Fruchterman and Reingold's layout) (FIG. 11b), Tulip (GEM layout) (FIG. 11c), and Tulip (Speing-Electrical Force layout) (FIG. 11d)
Figure 11B:
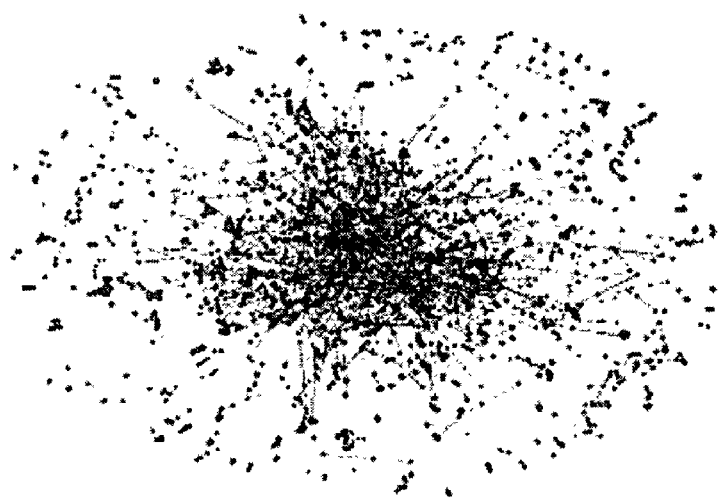
Figure 11C:
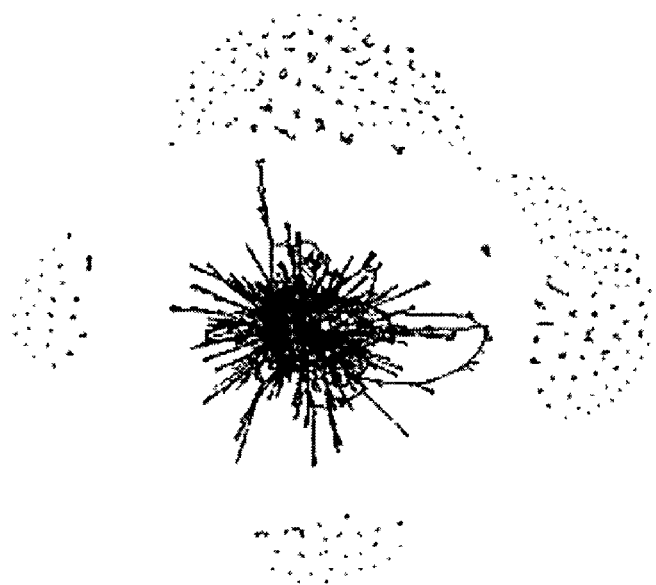
Figure 11D:

A graph visualized by InterViewer can be simplified by limiting distance level of neighbors. For example, when the distance level of neighbors of CIT2 is set as 5, InterViewer finds a reduced graph with 76 nodes, as shown in FIG. 8. In this graph, SEP2, PAN1 and FIR1, which are nodes selected by the user, can be indicated in different colors, and CIT2 can be indicated in a different color, thus offering convenience to the user. The user can choose to fix positions of one or more nodes during the force-directed layout. After the initial layout, the node positions of a star-shaped subgraph produced by fixing the center of the subgraph usually generates a satisfactory graph.

As described hereinbefore, the method of visualizing protein interaction data according to the present invention can implement a program which visualizes large-scale protein interaction networks into a clear and aesthetically pleasing drawing, and is over 10 times faster than the conventional force-directed algorithms. To compare running times, the two conventional graph-drawing programs, Pajek (Batagelj & Mrvar, 2001) and Tulip (David, 2001), were run. In Pajek, three algorithms including Kamada & Kawai's algorithm (1989), Eigen value method (Golub & van Loan, 1996), and Fruchterman & Reingold's algorithm (1991) were implemented for layout. Since Kamada & Kawai's algorithm does not produce a disconnected graph and produces only a two-dimensional graph, and Eigen value method does not give a graph-drawing result as good as that by Fruchterman & Reingold's algorithm, only Fruchterman & Reingold's algorithm was used for experimental comparison. In addition, we select two layout algorithms, Spring-Electric Force layout and GEM algorithm of Tulip. Table 1 shows the running times of InterViewer, Pajek and Tulip on a same set of test cases on a Pentium IV 1.7 Ghz processor. And, the resulting drawing by InterViewer, Pajek (Fruchterman-Reingold) and Tulip (Spring-Electric) & Tulip (GEM) are given in FIGS. 9a to 11d, respectively.

TABLE 1

| Program (layout algorithm) | Y2H data (1005 nodes, 905 edges) | MIPS genetic interaction data (888 nodes, 1093 edges) | MIPS physical interaction data (2167 nodes, 2948 edges) |
|---|---|---|---|
| InterViewer | 5 s | 5 s | 23 s |
| Pajek (Fruchterman-Reingold) | 3 m 17 s | 1 m 48 s | 12 m 42 s |
| Tulip (GEM) | 26 s | 19 s | 27 m 0 s |
| Tulip (Spring-Electric) | 3 m 40 s | 3 m 43 s | 95 m 21 s |

In addition, the method for visualization according to the present invention can be used for finding and exploring individual connected components or subgraphs interactively, as well as visualizing protein interactions. Moreover, the method for visualization can provide an integrated framework for dynamically querying protein interaction database and directly visualizing the query results, thus facilitating visualization and analysis of a large volume of updated data.

The invention claimed is:

1. A method for visualizing large-scale protein interaction data on a display by use of a computer, comprising the steps of:

producing an initial layout by placing all proteins of protein interaction data as nodes on the surface of a sphere by increasing a horizontal angle (theta) and a vertical angle (phi) of each node in polar coordinates according to the following algorithm:

```
1:  θ_increment = 2π/√n          {n: number of nodes}
2:  φ_increment = 2π/n
3:  θ = 0, φ = 0
4:  for v ∈ V do
5:     pos[v] = (r, θ, φ)         {r: radius of a sphere}
6:     θ = θ + θ_increment
7:     φ = φ + φ_increment
8:  end for; and
``` yielding a three-dimensional graph by iterating a predetermined number of times a process of moving each node of the initial layout to an equilibrium position and updating node positions based on spring forces between a non-adjacent nodes and the node of the initial layout as well as spring forces between an adjacent nodes and the node of the initial layout, wherein the three-dimensional graph is yielded through the following algorithm:

```
1:  r = 1
2:  repeat
3:     g = 0.01 · r · k²          {k: natural spring length}
4:     for v ∈ V do
5:        D = 0                   {D: displacement vector of v}
6:        for u ∈ V, u ≠ v do
7:           Δ = pos[u] − pos[v]  {pos[u]: position of node u}
8:           D = D − g · (Δ/|Δ|) · (|u|/|Δ|)
                                  {|u|: distance of u from the origin}
9:           if u ∈ Γ(v) then
10:             D = D − Δ/|Δ| · (1 − |Δ|/k)/|Γ(v)|
                                  {Γ(v): set of nodes adjacent to v}
11:          end if
12:       end for
13:       pos[v_new] = pos[v_old] + D
14:    end for
15:    r = 0.98 · r
16: until T times               {T: user-determined number or 20 by default}.
```

2. The method as set forth in claim 1, wherein the process of moving each node is iterated by a number of times decided by a user.

3. The method as set forth in claim 1, wherein the protein interaction data is yeast two hybrid (Y2H) data, Martinsried Institute for Protein Sequences (MIPS) genetic interaction data or MIPS physical interaction data.

4. The method as set forth in claim 1, further comprising the step of simplifying the graph by limiting a distance between a node selected by a user and nodes neighboring to the node to a predetermined distance.

* * * * *